United States Patent
Ma et al.

(10) Patent No.: US 11,495,357 B2
(45) Date of Patent: *Nov. 8, 2022

(54) METHOD AND DEVICE FOR AUTOMATICALLY PREDICTING FFR BASED ON IMAGES OF VESSEL

(71) Applicant: SHENZHEN KEYA MEDICAL TECHNOLOGY CORPORATION, Shenzhen (CN)

(72) Inventors: Bin Ma, Bellevue, WA (US); Ying Xuan Zhi, Seattle, WA (US); Xiaoxiao Liu, Bellevue, WA (US); Xin Wang, Seattle, WA (US); Youbing Yin, Kenmore, WA (US); Qi Song, Seattle, WA (US)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/107,881

(22) Filed: Nov. 30, 2020

(65) Prior Publication Data

US 2021/0082580 A1 Mar. 18, 2021

Related U.S. Application Data

(63) Continuation of application No. 16/048,272, filed on Jul. 28, 2018, now Pat. No. 10,937,549.

(Continued)

(51) Int. Cl.
*G16H 50/50* (2018.01)
*A61B 5/0275* (2006.01)
(Continued)

(52) U.S. Cl.
CPC ........... *G16H 50/50* (2018.01); *A61B 5/0261* (2013.01); *A61B 5/0263* (2013.01);
(Continued)

(58) Field of Classification Search
None
See application file for complete search history.

(56) References Cited

U.S. PATENT DOCUMENTS

| 10,249,048 B1 | 4/2019 | Wang et al. |
| 10,331,852 B2 | 6/2019 | Dormer et al. |

(Continued)

FOREIGN PATENT DOCUMENTS

| CN | 104854592 A | 8/2015 |
| CN | 106037710 A | 10/2016 |

(Continued)

OTHER PUBLICATIONS

First Office action issued in related Chinese Application No. 201910329859.X, dated Sep. 2, 2020, 12 pages.

*Primary Examiner* — Delomia L Gilliard
(74) *Attorney, Agent, or Firm* — Bayes PLLC (57) ABSTRACT

The present disclosure is directed to a method and system for automatically predicting a physiological parameter based on images of vessel. The method includes receiving the images of a vessel acquired by an imaging device. The method further includes determining a sequence of temporal features at a sequence of positions on a centerline of the vessel based on the images of the vessel, and determining a sequence of structure-related features at the sequence of positions on the centerline of the vessel. The method also includes fusing the sequence of structure-related features and the sequence of temporal features at the sequence of positions respectively. The method additionally includes determining the physiological parameter for the vessel at the sequence of posi- (Continued)

tions, by using a sequence-to-sequence neural network configured to capture sequential dependencies among the sequence of fused features.

20 Claims, 8 Drawing Sheets

Related U.S. Application Data (60) Provisional application No. 62/674,608, filed on May 22, 2018.

(51) Int. Cl.
*A61B 5/026* (2006.01)
*A61B 6/00* (2006.01)
*A61B 6/03* (2006.01)
*G06T 7/00* (2017.01)
*A61B 5/02* (2006.01)

(52) U.S. Cl.
CPC ............ *A61B 5/0275* (2013.01); *A61B 6/504* (2013.01); *A61B 6/5217* (2013.01); *A61B 5/02007* (2013.01); *A61B 6/032* (2013.01); *A61B 6/481* (2013.01); *G06T 7/0012* (2013.01); *G06T 2207/20081* (2013.01); *G06T 2207/30048* (2013.01); *G06T 2207/30104* (2013.01)

(56) References Cited

U.S. PATENT DOCUMENTS

| | | |
|---|---|---|
| 2013/0266184 A1 | 10/2013 | Patwardhan et al. |
| 2014/0073977 A1 | 3/2014 | Grady et al. |
| 2014/0200867 A1 | 7/2014 | Lavi et al. |
| 2014/0243662 A1 | 8/2014 | Mittal et al. |
| 2015/0065864 A1 | 3/2015 | Sharma et al. |
| 2015/0112182 A1 | 4/2015 | Sharma et al. |
| 2016/0338613 A1 | 11/2016 | Beckers et al. |
| 2017/0076043 A1* | 3/2017 | Dormer ............... G06F 21/6218 |
| 2018/0092616 A1* | 4/2018 | Sakaguchi ............ G16H 30/40 |
| 2019/0130578 A1* | 5/2019 | Gulsun ............... G06N 3/0445 |
| 2019/0298311 A1 | 10/2019 | Haase et al. |
| 2020/0037982 A1 | 2/2020 | Van Der Horst et al. |

FOREIGN PATENT DOCUMENTS

| | | |
|---|---|---|
| CN | 106456078 A | 2/2017 |
| CN | 106980899 A | 7/2017 |
| CN | 107545269 A | 1/2018 |

* cited by examiner

METHOD AND DEVICE FOR AUTOMATICALLY PREDICTING FFR BASED ON IMAGES OF VESSEL

CROSS-REFERENCE TO RELATED APPLICATIONS

This application is a continuation of U.S. application Ser. No. 16/048,272 filed Jun. 28, 2018, which claims the benefit of priority to U.S. Provisional Application No. 62/674,608, filed on May 22, 2018, the entire contents of which are incorporated herein by reference.

TECHNICAL FIELD

The disclosure generally relates to image processing and analysis. More specifically, this disclosure relates to method and device for automatically predicting fractional flow reserve (FFR) based on images of vessel.

BACKGROUND

Coronary circulation supplies oxygen to heart muscles (myocardium) via circulating blood in the coronary arteries. A severe coronary artery stenosis can limit myocardial blood flow and result in myocardial ischemia. Coronary X-ray angiography is one of the most common techniques for diagnosing coronary heart disease. By injecting a contrast agent that is partially opaque to X-ray into a blood vessel, X-ray angiography can dynamically observe, from different orientations (i.e., from different projection view angles), the shape and state of the vessel and any lesions thereof, as well as flow dynamics. X-ray angiography is generally adapted for examining large vessels of the heart, such as a coronary artery, as well as cervical and intracranial arteries, and is often used for diagnosing and observing arterial stenosis, occlusion, blood vessel development abnormality and blood supply conditions. However, the degree of stenosis is evaluated manually by the medical staff (such as a radiologist) viewing such images, the accuracy of which depends on the experience of the medical staff. Besides, the medical staff cannot directly evaluate blood flow supply and ischemic condition at the distal end of a blood vessel tree only on the basis of the degree of stenosis. The Fractional Flow Reserve (FFR) has been proposed in 1995 and has become an important index for evaluating coronary blood flow and guiding the decision of coronary revascularization. However, FFR measurement is made by using a pressure guide wire in an invasive manner and may even cause risks of trauma especially when being performed frequently.

Vessel simulation has been introduced, which mainly depends on physics models, such as computational fluid dynamics (CFD) solvers or empirical fluid dynamic equations, to compute the FFR in the vessel. These vessel simulation approaches rely heavily on assumptions of blood fluid properties, vessel and stenosis geometries, and thus may result in prediction error. For example, virtually calculating FFR (virtual FFR) was developed in favor of its non-invasive nature, and to potentially reduce patient's diagnostic discomfort and cost. At present, virtual FFR methods mainly include $FFR_{CT}$ based on coronary angiography CT, FFR simulation vFFR based on X-ray angiography image, and $FFR_{QCA}$ based on the combination of quantitative coronary angiography with a TIMI (Thrombolysis In Myocardial Infarction) frame count method. CFD approach often requires tens of minutes or even hours of simulation time and cannot be applied for real-time usage. Approach using empirical fluid dynamic equations makes several assumptions about the fluid properties and vessel geometries, is limited to certain conditions (such as, vessel curvature cannot be too large), and thus is not expandable due to the underlying assumptions and is not accurate enough under various conditions.

Machine learning based method can be used to provide fast and data-oriented approach of predicting FFR values. However, the existing method usually uses manually designed features, which needs to be adapted to various conditions and different patients, since the prediction accuracy depends on the design of the features.

Additionally, the performance of the existing machine learning based method is ultimately limited by the training data. And the calculation results provided by vessel simulation (such as CFD simulation) are often adopted as training data for the learning network. However, the errors in the physical model of the vessel simulation will be copied and maintained in the trained learning network, which degrades its performance.

A method and device for automatically predicting fractional flow reserve (FFR) based on images of vessel is disclosed to address the above concerns.

SUMMARY

This disclosure provides a method and device for automatically predicting fractional flow reserve (FFR) based on images of vessel. This method may be deployed for real-time usage, adopts convolutional neural network (CNN) as feature extractor and fusing both structure-related features and flow speeds to obtain the features, and is thus potentially more friendly and powerful than existing method based on only manual designed features. Further, this method makes good use of invasively measured FFR to obtain training data more consistent with ground truth data, and thus increases the prediction accuracy. Besides, this method feeds the sequence of fused features along the vessel to a sequence-to-sequence network, so as to take the mutual influences of the points along the vessel into account and thus further increase the prediction accuracy.

In one aspect, the present disclosure is directed to a computer-implemented method for automatically predicting a physiological parameter based on images of vessel. The method includes receiving the images of a vessel acquired by an imaging device. The method further includes determining a sequence of temporal features at a sequence of positions on a centerline of the vessel based on the images of the vessel, and determining a sequence of structure-related features at the sequence of positions on the centerline of the vessel. The method also includes fusing the sequence of structure-related features and the sequence of temporal features at the sequence of positions respectively. The method additionally includes determining the physiological parameter for the vessel at the sequence of positions, by using a sequence-to-sequence neural network configured to capture sequential dependencies among the sequence of fused features.

In another aspect, the present disclosure is directed to a system for automatically predicting a physiological parameter based on images of vessel. The system includes an interface configured to receive the images of the vessel acquired by an imaging device. The device also includes a processor. The processor is configured to determine a sequence of temporal features at a sequence of positions on a centerline of the vessel based on the images of the vessel, and determine a sequence of structure-related features at the sequence of positions on the centerline of the vessel. The processor is further configured to fuse the sequence of structure-related features and the sequence of temporal features at the sequence of positions respectively. The processor is also configured to determine the physiological parameter for the vessel at the sequence of positions, by using a sequence-to-sequence neural network configured to capture sequential dependencies among the sequence of fused features.

In still another aspect, the present disclosure is directed to a non-transitory computer readable medium having instructions stored thereon. The instructions, when executed by a processor, perform a method for automatically predicting a physiological parameter based on images of vessel. The method includes receiving the images of a vessel acquired by an imaging device. The method further includes determining a sequence of temporal features at a sequence of positions on a centerline of the vessel based on the images of the vessel, and determining a sequence of structure-related features at the sequence of positions on the centerline of the vessel. The method also includes fusing the sequence of structure-related features and the sequence of temporal features at the sequence of positions respectively. The method additionally includes determining the physiological parameter for the vessel at the sequence of positions, by using a sequence-to-sequence neural network configured to capture sequential dependencies among the sequence of fused features.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, system, or non-transitory computer readable medium having instructions thereon for implementing the method.

DETAILED DESCRIPTION

Hereinafter, the technical term "feature" may be any one of a matrix, vector, and numeral value that may be used as an input of a neural network or a part of it. Further, the technical term "structure-related feature" may mean feature associated with the structure of the vessel. The "structure-related feature" may include feature (referred to as "structural feature" hereinafter) having a definite structural and physical meaning which may be easily understood by the medical staff, such as vessel radius, reference radius (the radius of the diseased vessel as if it is under healthy condition (e.g. there is no narrowing due to stenosis)), curvature, depth of optical path, etc. Besides, the "structure-related feature" may also include feature, e.g. a feature obtained by feeding image or structural feature into a CNN, that imply (encode) structural information (which means that the medical staff cannot extract and understand such encoded structural information from the feature), and the encoded structural information may include any one of vessel radius, reference radius (the radius of the diseased vessel as if it is under healthy condition (e.g. there is no narrowing due to stenosis)), curvature, depth of optical path, etc. or the combination thereof. The technical term "optical path" means the ray transmission path. Besides, the technical term "image of vessel" may mean the image including the vessel portions. For example, the "image of vessel" may be an image of a target site, with vessel portion and other contents (such as other organs and the background portion) therein.

Figure 1:
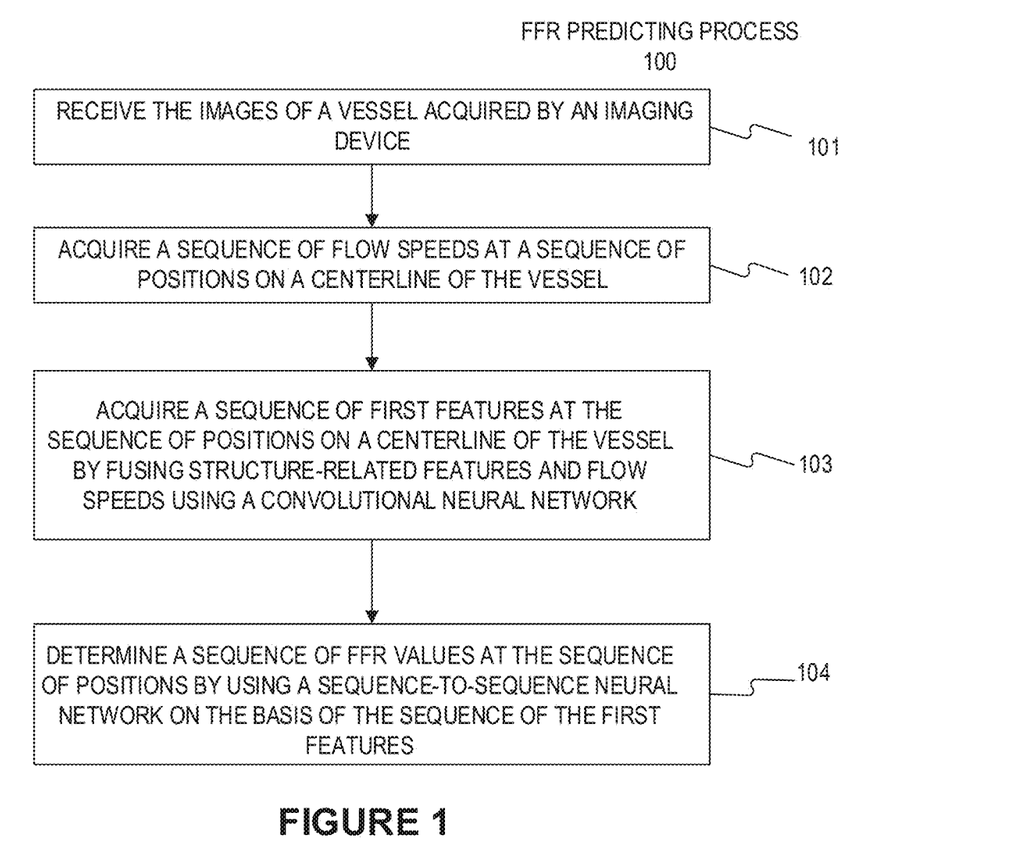
FIG. 1 illustrates an exemplary FFR prediction process according to an embodiment of present disclosure.

FIG. 1 illustrates an exemplary FFR predicting process 100 of a computer-implemented method for automatically predicting FFR based on images of a vessel according to an embodiment of present disclosure. As shown in FIG. 1, the FFR predicting process 100 may include the following steps: receiving the images of a vessel acquired by an imaging device (step 101); acquiring a sequence of flow speeds at a sequence of positions on a centerline of the vessel (step 102); acquiring a sequence of first features at the sequence of positions on a centerline of the vessel by fusing structure-related features and flow speeds and using a CNN (step 103); and determining a sequence of FFR values at the sequence of positions by using a sequence-to-sequence neural network on the basis of the sequence of first features (step 104).

In some embodiments, the sequence-to-sequence neural network may be selected from a group of a recurrent neural network (RNN), gated recurrent unit (GRU), long-short-term memory unit (LSTM) or their bidirectional variants. A RNN may be adopted as the sequence-to-sequence neural network, but the RNN may be replaced with other sequence-to-sequence neural networks as needed.

In some embodiments, the FFR predicting process 100 may adopt a CNN-sequence-to-sequence network learning network, wherein the CNN is used as feature extractor to extract structure-related features, e.g. the CNN may be used to extract structure-related features from images or extract a higher level of structure-related features from manually designed structural features. By using the CNN, step 103 may extract structure-related features efficiently (acceleration effect of convolutional operation on the image) and adaptively (through training of the learning network including CNN), and thus it may be less prone to over fitting due to parameter sharing of the CNN. In some embodiments, the parameters of the CNN may be tuned automatically by training, thus the medical staff does not need to manually design and modify feature depending on the application scenes of the learning network. For example, the medical staff may simply design a fixed structural feature matrix including vessel radius, reference radius, etc. of a sequence of points on the vessel centerline, feed this structural feature matrix into a CNN to extract higher level structure-related features, and use training data to train the CNN to adapt the extracted structure-related features to the application scenes. In this manner, the work load of the medical staff is greatly alleviated, which facilitates the expanding of the automatic FFR predicting method.

In some embodiments, the fusing of the structure-related features and flow speeds at the sequence of positions on the centerlines of the vessel may be carried out before or after applying the CNN in the prediction pipeline. By fusing both the structure-related features and flow speeds meanwhile using the sequence-to-sequence network (which may take mutual influences between different positions on the centerline into account), the FFR prediction model simulates accurately and comprehensively the physical acting mechanism of the FFR, and thus improve the performance of the FFR prediction method. In clinical experiments, the inventor confirmed that the performance of the FFR prediction method of present disclosure precedes that utilizing separate structure-related features or separate flow speed as features and that utilizing point-to-point learning network instead of sequence-to-sequence network. Besides, the FFR prediction method of present disclosure may predict FFR values and map the same back to the vessel centerline and the 3D vessel geometry, nearly in real-time.

Figure 2:
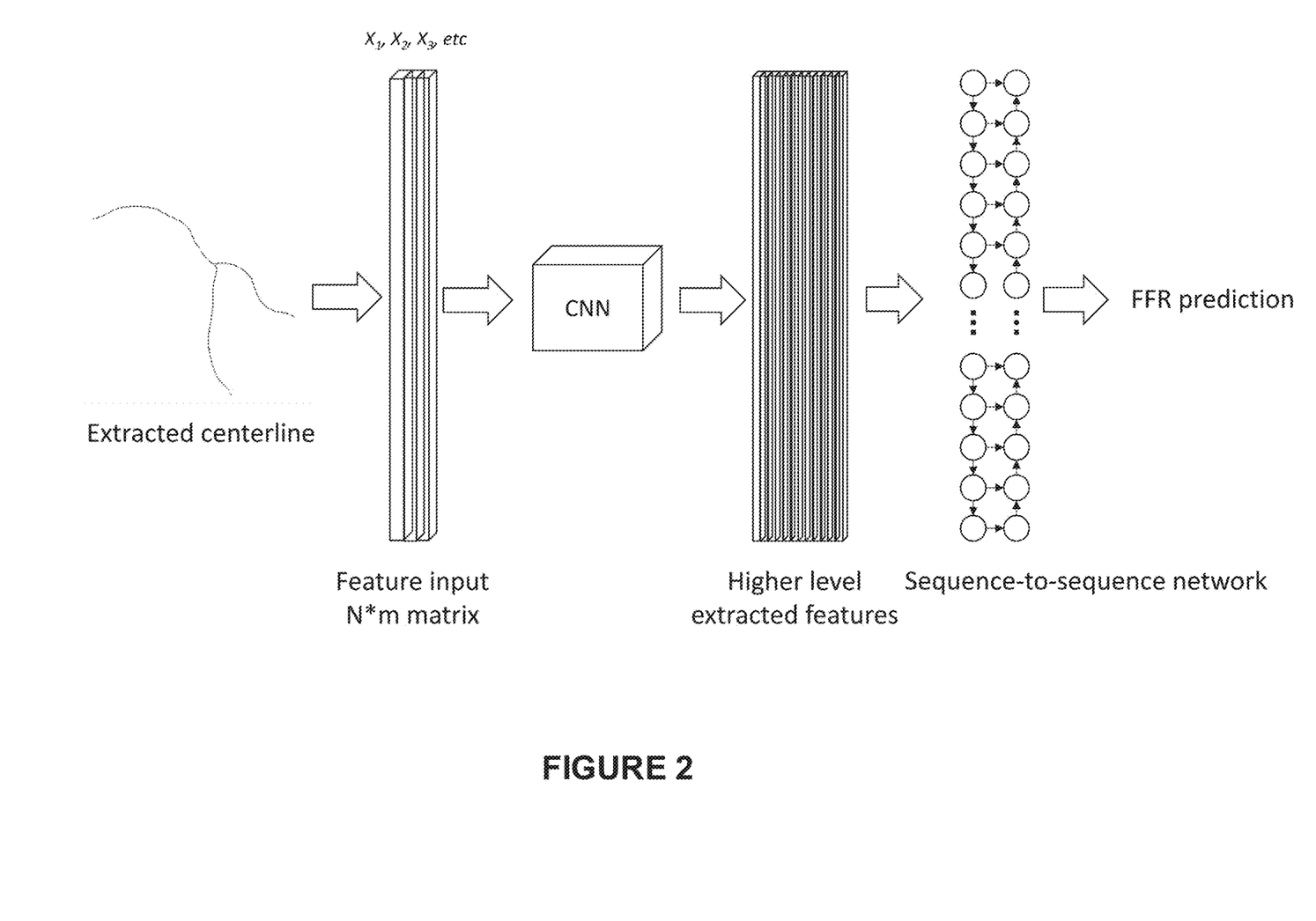
FIG. 2 illustrates an exemplary process for predicting a sequence of FFR values on a 3D centerline of a vessel using a first pipeline of CNN-sequence-to-sequence network, according to an embodiment of present disclosure.

The vessel centerline may be a 3D centerline or a 2D centerline. FIG. 2 illustrates an exemplary process for predicting a sequence of FFR values on a 3D centerline of a vessel according to an embodiment of present disclosure, wherein a first pipeline of CNN-sequence-to-sequence network is adopted as the learning network.

As shown by FIG. 2, the predicting process begins with extracting a 3D centerline and the corresponding structural features at the sequence of positions on the 3D centerline. Particularly, it may include reconstructing a 3D model of the vessel on the basis of the at least two images of the vessel from different projection view angles and extracting the 3D centerline of the vessel. The 3D reconstruction may be carried out as follows: extracting 2D centerlines and vessel walls from the sequence of 2D vessel images and reconstruction of the 3D vessel model including the 3D centerline on the basis of the same. Then, from the 3D vessel model, a sequence of structural features at the sequence of positions on the 3D centerline may be acquired, including but not limited to at least one of vessel radius, reference radius, curvature, and depth of optical path. In some embodiments, the sequence of flow speeds at the sequence of positions on the 3D centerline may be derived from an automatic frame counting procedure. In some embodiments, various other procedures may be adopted to obtain the sequence of flow speeds, including but not limited to the procedure disclosed by U.S. Provisional Application No. 62/591,437, filed on Nov. 28, 2017.

Each of the structural features and flow speeds may be treated as one channel. As shown in FIG. 2, the input matrix has a dimension of N*m where N is the number of positions (points) on the 3D centerline and m is the number of channels (i.e., features). For example, each column vector of the feature matrix, i.e., $X_1$, X2, X3 . . . represents the corresponding sequence of features at the sequence of positions on the 3D centerline, wherein one column vector represents the sequence of flow speeds at the sequence of positions on the 3D centerline. The input matrix is fed into a CNN to extract higher level features. In some embodiments, the CNN block can be composed with several convolution layers with proper padding followed by non-linear activation units. In some embodiments, the activation units may be sigmoid, tanh or rectified linear units (relu). The extracted features (i.e., outputs from the CNN block) form N nodes that are sequentially connected, and each node corresponds to the centerline point in the middle of the node's receptive field. The sequence of the nodes is then fed into a sequence-to-sequence network for sequence-to-sequence prediction. The sequence-to-sequence network are good at capturing the sequential dependencies between downstream nodes and upstream nodes, thus improves the performance of the predicting process. In some embodiments, RNN may be adopted as the sequence-to-sequence neural network. In other embodiment, any one of GRU, LSTM, or their bidirectional variants may be adopted as the sequence-to-sequence neural network, so as to solve the numerical problems, such as gradient exploding and gradient vanishing, in learning long term dependencies encountered in vanilla RNN.

Figure 3:
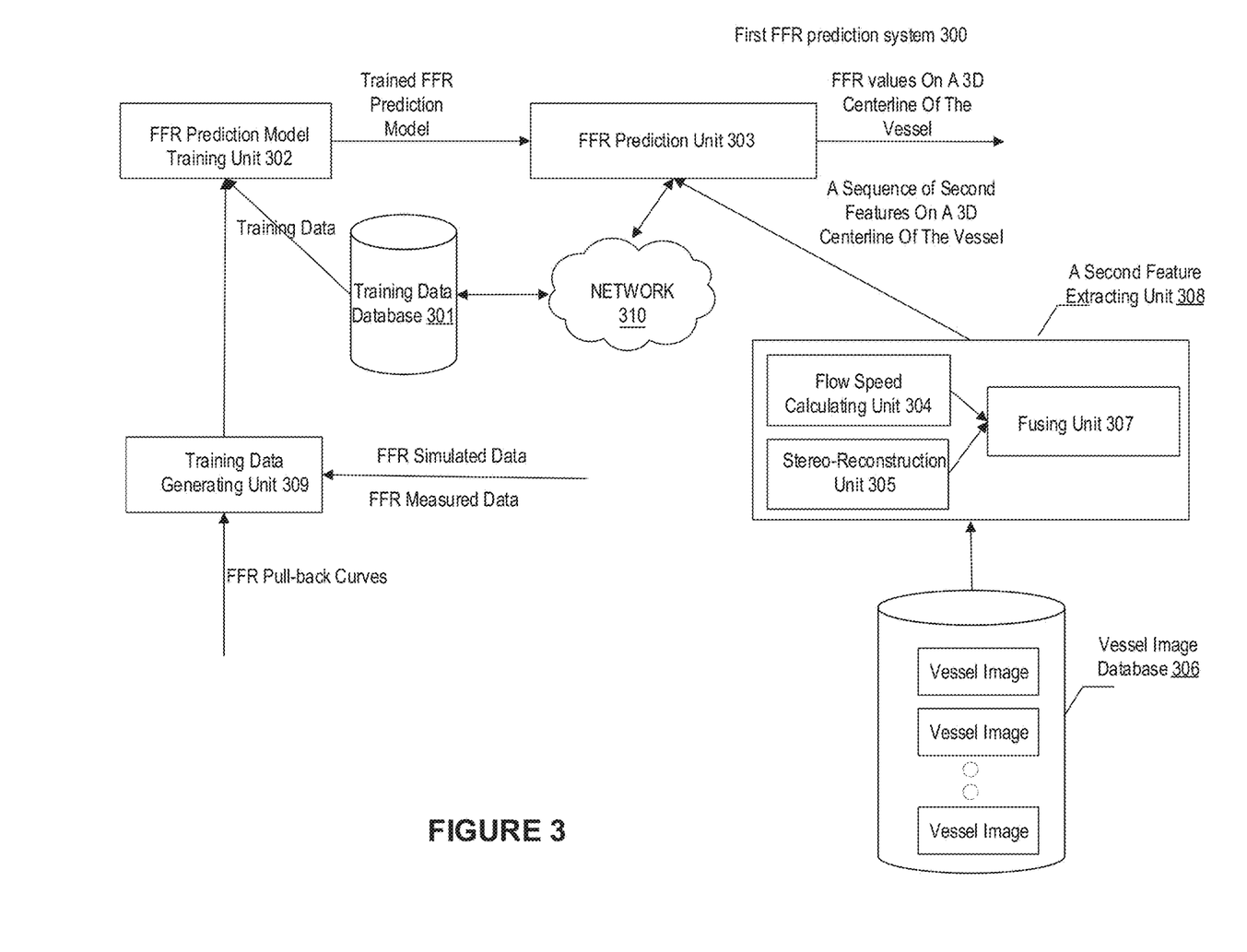
FIG. 3 illustrates a first FFR prediction system adapted to perform the predicting process as shown in FIG. 2, according to an embodiment of present disclosure.

FIG. 3 illustrates a first FFR prediction system 300 according to an embodiment of present disclosure, which is adapted to perform the predicting process as shown in FIG. 2. As shown in FIG. 3, the first FFR prediction system 300 may include a second feature extracting unit 308, a FFR prediction model training unit 302, and a FFR prediction unit 303. In some embodiments, the second feature extracting unit 308 may receive vessel images from a vessel image database 306, and feed the same to a flow speed calculating unit 304 and a stereo-reconstruction unit 305. The stereo-reconstruction unit 305 may carry out 2D image processing on the received vessel images and stereo-reconstruction, so as to extract the 2D centerline of each 2D vessel images, 3D centerline of the 3D vessel geometry, and the structural features along the 3D centerline. The flow speed calculating unit 304 may derive flow speeds along the 3D centerline. In some embodiments, the flow speed calculating unit 304 may derive flow speeds along the 2D centerlines of the vessel images with e.g. an automatic frame counting procedure and map the derived flow speeds to respective positions on the 3D centerline, so as to obtain flow speeds along the 3D centerline. The sequence of flow speeds and structural features are fused by the fusing unit 307 to obtain a sequence of second features along the 3D centerline. In some embodiments, the fusing operation may be carried out by concatenating each sequence of structural features altogether with the sequence of flow speeds as shown in FIG. 2 to obtain a feature matrix with each node corresponding to a respective position on the 3D centerline.

The sequence of the second features on the 3D centerline is fed to the FFR prediction unit 303 to predict the sequence of FFR values on the 3D centerline of the vessel by using the trained FFR prediction model received from the FFR prediction model training unit 302. In some embodiments, the FFR prediction model training unit 302 may be configured to train the FFR prediction model (e.g. the first pipeline of CNN-sequence-to-sequence neural network) by using training data. In some embodiments, the training data may be obtained from a training data database 301 or generated by a training data generating unit 309. In some embodiments, the sequence of second features on the 3D centerline and the predicted sequence of FFR values may be transmitted from the FFR prediction unit 303 to the training data database 301 as new samples via a network 310, so as to update the training data database 301. In this manner, the training data may be enriched continuously by the prediction processes and the performance of the trained FFR prediction model may benefit from the enriched training data.

The training data generating unit 309 may be configured to generate the training data via various methods as follows.

In some embodiments, FFR values along the vessel centerline, which are e.g. simulated from physics-based models such as CFD or empirical fluid dynamic equations, are used directly as the training data. However, the physics-based models depend several assumptions about the fluid properties (blood density, viscosity), vessel geometries, etc., thus the simulated FFR values may be shifted from the actually measured FFR values. The FFR prediction model based on the learning network, which is trained using the simulated FFR values, is essentially a surrogate model for the physics-based models. The FFR prediction model based on the learning network provides a much faster prediction than the physics-based models, but it cannot compensate the errors in the physics-based models and thus is not accurate enough.

The measured FFR values along the vessel centerline may be the best candidate for ground truth data. However, for a vessel, the pressure at its distal end is usually measured by a pressure sensor on a pressure wire and divided by the aortic pressure to obtain a single FFR value instead of a sequence of FFR values. FFR pull-back curves provides the measured FFR along the blood vessel centerline. However, the FFR pull-back curves are not available for a great amount of data, thus cannot serve as the training data independently.

In some embodiments, the measured FFR values are used to correct the simulated FFR results to generate the training data. Particularly, correcting the simulated FFR results by using measured FFR values includes stretching and/or translating the simulated FFR results to make the simulated FFR value at a measurement point on the centerline equal to the corresponding measured FFR value meanwhile respecting the gradient of the simulated FFR results. In this manner, the corresponding measured FFR value may be used as a reference to correct the drifting of the simulated FFR results with respect to the measured FFR results. Besides, the characteristics of the profile of the measured FFR results may be reflected by the gradient of the simulated FFR results, thus stretching the profile of the simulated FFR results in consideration of the gradient thereof may obtain a profile of the corrected FFR results approximating that of the measured FFR results.

Figure 4:
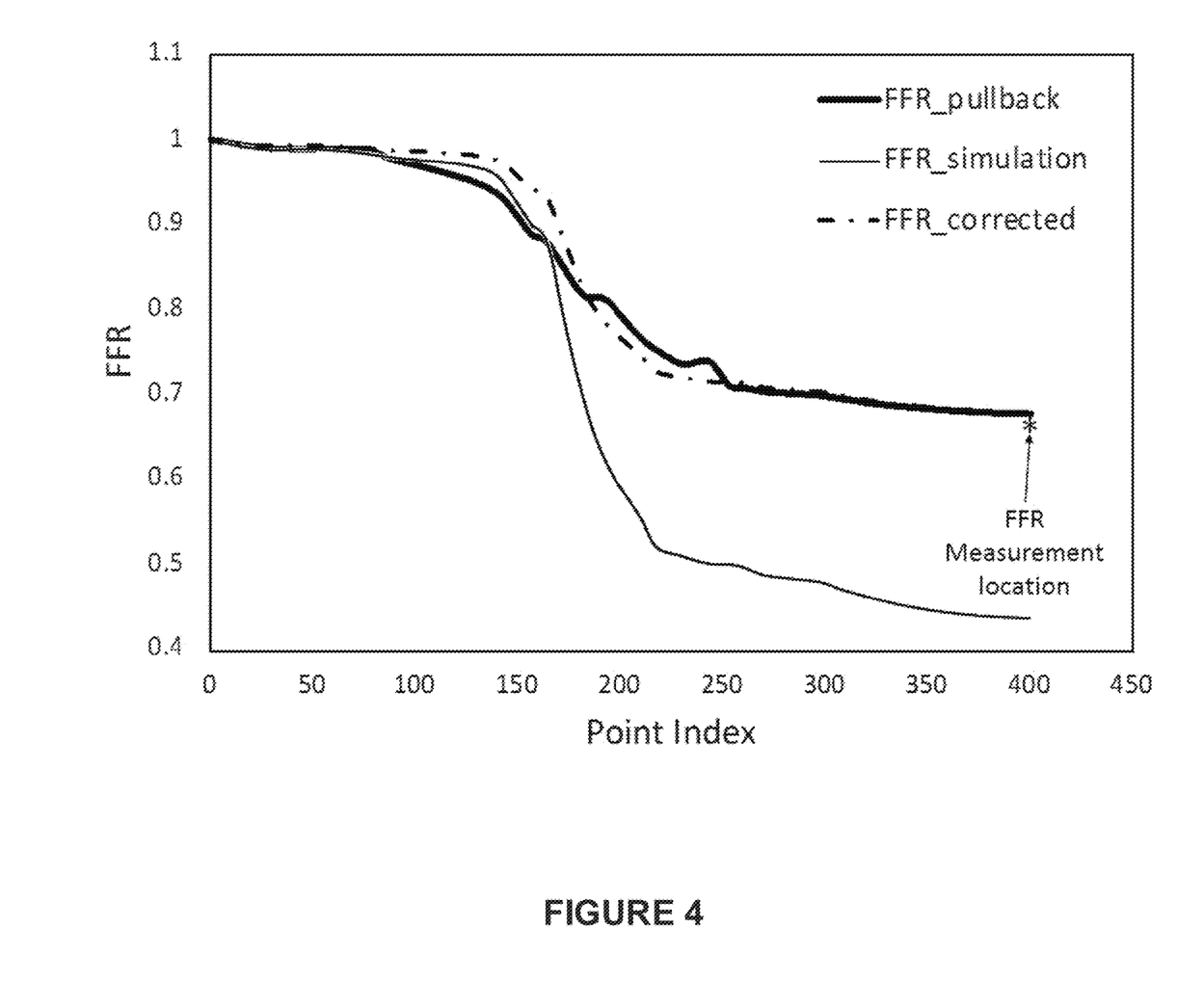
FIG. 4 illustrates a profile of simulated FFR values along a vessel vs. a profile of corrected FFR values along the vessel according to an embodiment of present disclosure.

As shown in FIG. 4, the profile of measured FFR values along a vessel (e.g. obtained by a measured pull-back curve) differs from the profile of simulated FFR values; the measurement point is set at a distal end of the vessel so as to locate the diseased section on its proximal side. On the distal side of the measurement point, both the profile of simulated FFR values and the profile of the measured FFR values declines slowly at a nearly equal gradient (slope) as they go away from the measurement point. That is to say, on the distal side of the measurement point, the profile of simulated FFR values may be translated to unify the corrected FFR value at the measurement point with the measured FFR value at the measurement point. In this manner, the sectional profile of simulated FFR values on the distal side of the measurement point, after being translated, conforms to the sectional profile of the measured FFR values on the distal side of the measurement point. On the proximal side of the measurement point, the sectional profile of the simulated FFR values is stretched by maintaining the varying rate of the gradient of the simulated FFR results at the respective points on the vessel centerline. As shown in FIG. 4, the sectional profile of the simulated FFR values on the proximal side of the measurement point, after being stretched, conforms to that of the profile of the measured FFR values nicely on the proximal side of the measurement point. Although only one measurement point is used in FIG. 4 as example, a number of measurement points may be used as references, especially when the vessel has diffuse lesions or multiple lesions, so as to ensure the conformance of the corrected FFR results with the measured FFR results. In some embodiments, the centerline of the vessel may be divided by multiple measurement points into several sections and multiple sectional profiles of the simulated FFR values may be obtained accordingly, each sectional profile of the simulated FFR values may be stretched and translated separately to unify its value at the corresponding measurement point with the measured FFR value at the corresponding measurement point meanwhile maintaining the varying rate of the gradient thereof at the respective points on the corresponding section.

In some embodiments, the FFR pull-back curves, which are only available in temporal domain, may be mapped to vessel centerline point coordinates in the spatial domain by means of co-registration, so as to generate the corresponding training data. In some embodiments, the co-registration may be carried out as follows: setting a radiopaque mark at a predefined distance from the pressure sensor on the pressure wire, the existing portion or part of the pressure wire which is radiopaque may be used as the mark; during the pull-back process of the pressure wire, acquiring the pressure detection timing of each measured FFR value meanwhile tracking the positions of the radiopaque mark on the vessel centerline by sequentially imaging; determining the positions of the pressure sensor on the vessel centerline on the basis of the tracked positions of the radiopaque mark and the predefined distance. In some embodiments, the co-registration may be carried out in other technical means. For example, the radiopaque mark may be set at the pressure sensor, and a velocity sensor may be mounted at the proximal end of the pressure wire, once the reference coordinate of the radiopaque mark (the pressure sensor) on the centerline is determined (e.g., by means of image processing) from a reference image, the coordinates of the pressure sensor during the subsequent pull-back process may be automatically determined by subtracting the integration of the detected velocities between the detection timings from the reference coordinate.

Figure 5:
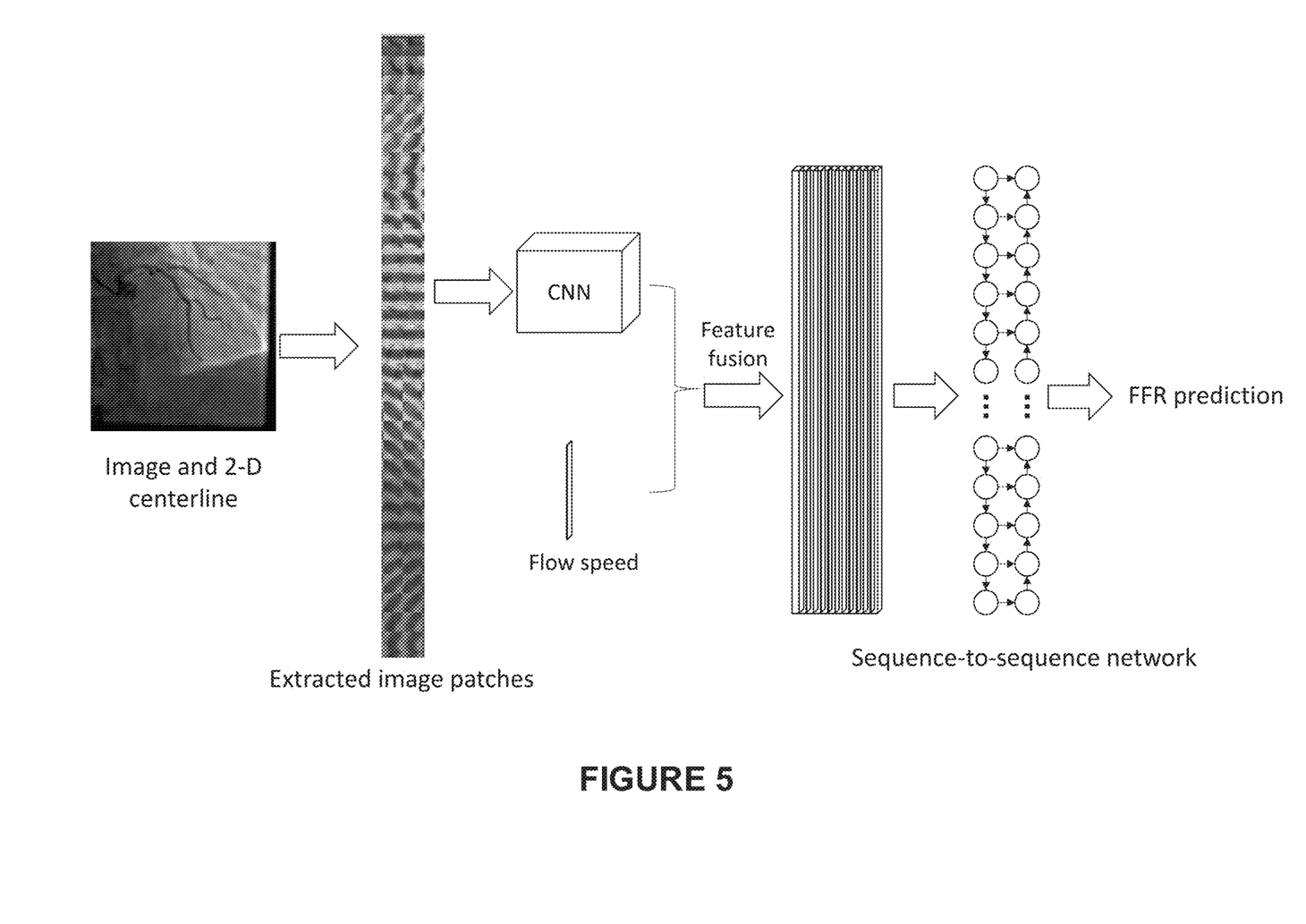
FIG. 5 illustrates an exemplary process for predicting a sequence of FFR values on a 2D centerline of a vessel using a second pipeline of CNN-sequence-to-sequence network, according to an embodiment of present disclosure.

FIG. 5 illustrates an exemplary process for predicting a sequence of FFR values on a 2D centerline of a vessel according to an embodiment of present disclosure, wherein a second pipeline of CNN-sequence-to-sequence network learning network is adopted as the learning network. As shown in FIG. 5, 2D images, especially a sequence of fixed sized image patches at a sequence of positions on the 2D centerline of the vessel, together with a sequence of flow speeds at the sequence of positions on the 2D centerline, are used as inputs. Compared to the inputs as shown in FIG. 2, the inputs are raw without post-treatment (such as for extracting structural features) and easier to obtain, thus the second pipeline is much friendlier to the medical staff.

For this embodiment, only extraction of 2D vessel centerline is needed, no 3D reconstruction is required for FFR prediction, thus accelerates the predicting process substantially. As a contrast, the existing FFR prediction process usually depends on 3D reconstruction of the vessel since those skilled in the art take it for granted that 2D images lack 3D information and that FFR prediction under the condition of losing 3D information may seem to be an ill-posed problem. However, the inventor found that local image intensity effectively encodes some important 3D information, such as optical path (as recorded in U.S. Provisional Application No. 62/592,595, filed on Nov. 30, 2017). The local image intensities in a sequence of fixed sized image patches sampled at a sequence of positions on the extracted 2D centerline of the vessel also encode important 3D information along the vessel centerline, thus the predicting process on the basis of the same still may have good performance with obviously reduced time consuming and simpler feature extraction.

In some embodiments, fix-sized (such as 30 pixel*30 pixel) image patches can be extracted sequentially along the centerline from proximal to distal. The sequence of image patches can be fed into the CNN (e.g. a 2D CNN block) to extract higher level features that encode rich information such as radius, depth of optical path, curvature and etc. These features can be further fused together with flow speed and be fed into the sequence-to-sequence network. The feature fusion can be performed simply by concatenation to form a bigger feature matrix. In some embodiments, the feature matrix may be acquired as follows: acquiring a sequence of the structure-related features by using the CNN on the basis of the sequence of fixed sized image patches; and fusing the sequence of structure-related features and the sequence of flow speeds at the sequence of positions on the 2D centerline of the vessel, so as to acquire the sequence of first features as the feature matrix. Similar to the predicting process as shown in FIG. 2, the step of fusing the sequence of structure-related features and the sequence of flow speeds comprises concatenating the structure-related feature and the flow speed at a corresponding position on a 2D centerline of the vessel, and each node of the feature matrix corresponds to a position on the 2D centerline of the vessel.

In some embodiments, for both the prediction processes as shown in FIG. 2 and FIG. 5, the CNN and the sequence-to-sequence neural network are trained integrally using the training data. However, the training data used for the predicting model as shown in FIG. 5 may be comprised of the sequence of image patches on the 2D centerline and the sequence of flow speeds on the 2D centerline vs. the FFR values on the 2D centerline. As a contrast, the training data used for the predicting model as shown in FIG. 2 may be the feature matrix obtained by fusing the sequence of structural features and the sequence of flow speeds at the sequence of positions on the 3D centerline vs. the FFR values on the 3D centerline.

Figure 6:
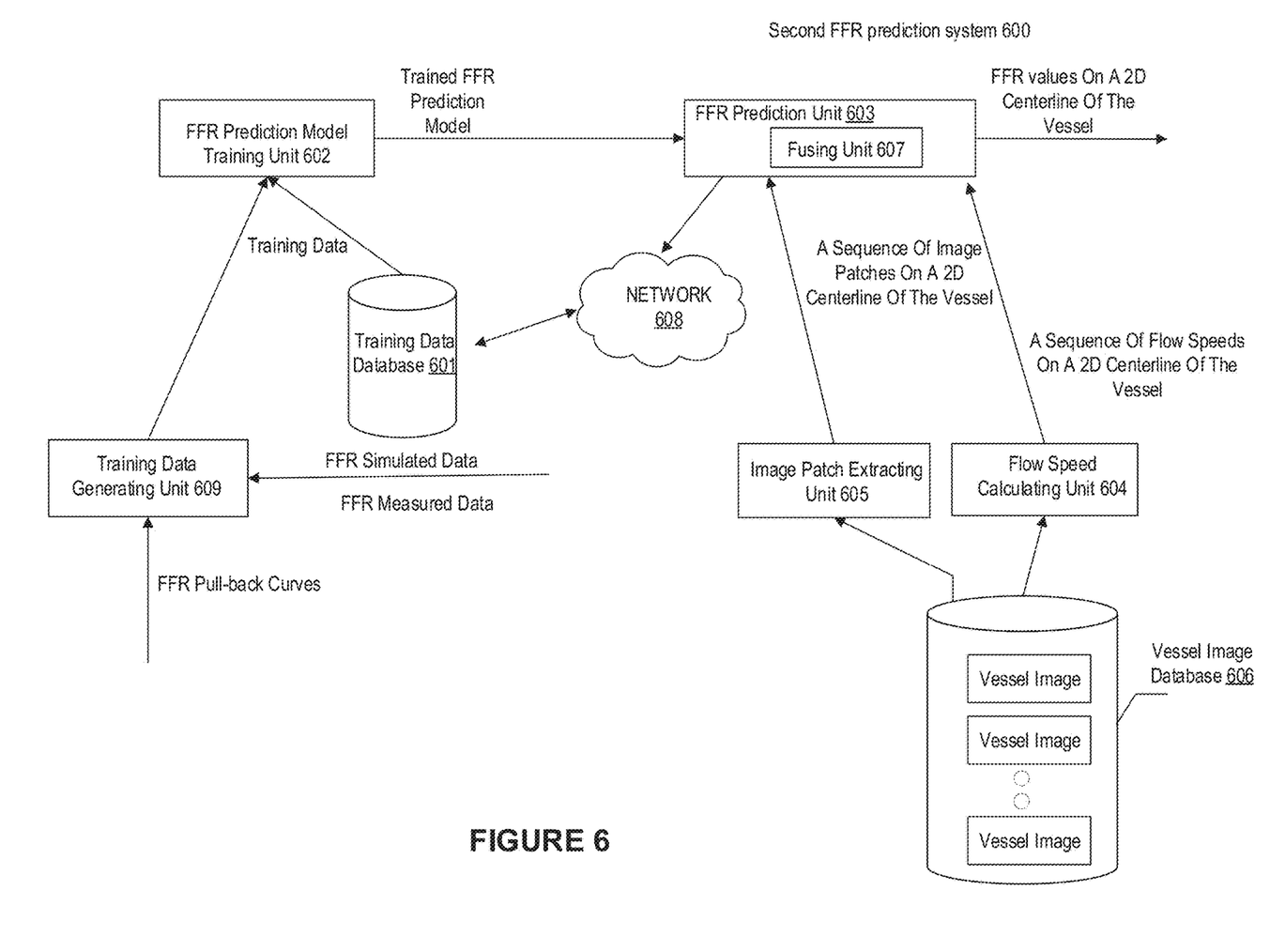
FIG. 6 illustrates a second FFR prediction system adapted to perform the predicting process as shown in FIG. 5, according to an embodiment of present disclosure.

FIG. 6 illustrates a second FFR prediction system according to an embodiment of present disclosure, which is adapted to the predicting process as shown in FIG. 5. Due to different prediction processes, the second FFR prediction system differs from the first FFR prediction system. Particularly, the vessel images are fed into an image patch extracting unit 605 to extract a sequence of image patches on a 2D centerline of the vessel, and are also fed into a flow speed calculating unit 604 to calculate a sequence of flow speeds on the 2D centerline similar to the described flow speed calculating unit 304 as shown in FIG. 3. Besides, a fusing unit 607 may be included inside instead of outside a FFR prediction unit 603. As shown in FIG. 6, an FFR prediction model training unit 602 may train the FFR prediction model with different training data from that adopted by the FFR prediction model training unit 302 and transmit the trained FFR prediction model (including the trained CNN and trained sequence-to-sequence neural network) to the FFR prediction unit 603. In some embodiments, the FFR prediction unit 603 may predict the FFR values on the 2D centerline of the vessel by performing fusing operation and using the trained CNN and sequence-to-sequence neural network on the basis of the sequence of image patches on the 2D centerline and the sequence of flow speeds on the 2D centerline as inputs. As an example, the FFR prediction unit 603 may apply the trained CNN to the sequence of image patches on the 2D centerline to extract a sequence of the structure-related features on the 2D centerline, which encode rich information such as radius, depth of optical path, curvature, etc., and fuse the same with the sequence of flow speeds on the 2D centerline, e.g., by concatenation, to acquire the sequence of first features, and then feed the acquired sequence of first features into the trained sequence-to-sequence neural network to obtain the FFR values on the 2D centerline as outputs.

The other units in FIG. 6, including the training data generating unit 609 and training data database 601, perform similar operations as that performed by corresponding units in FIG. 3, and thus the description thereof are omitted for avoiding redundancy and confusion with the core points of present disclosure.

Figure 7:
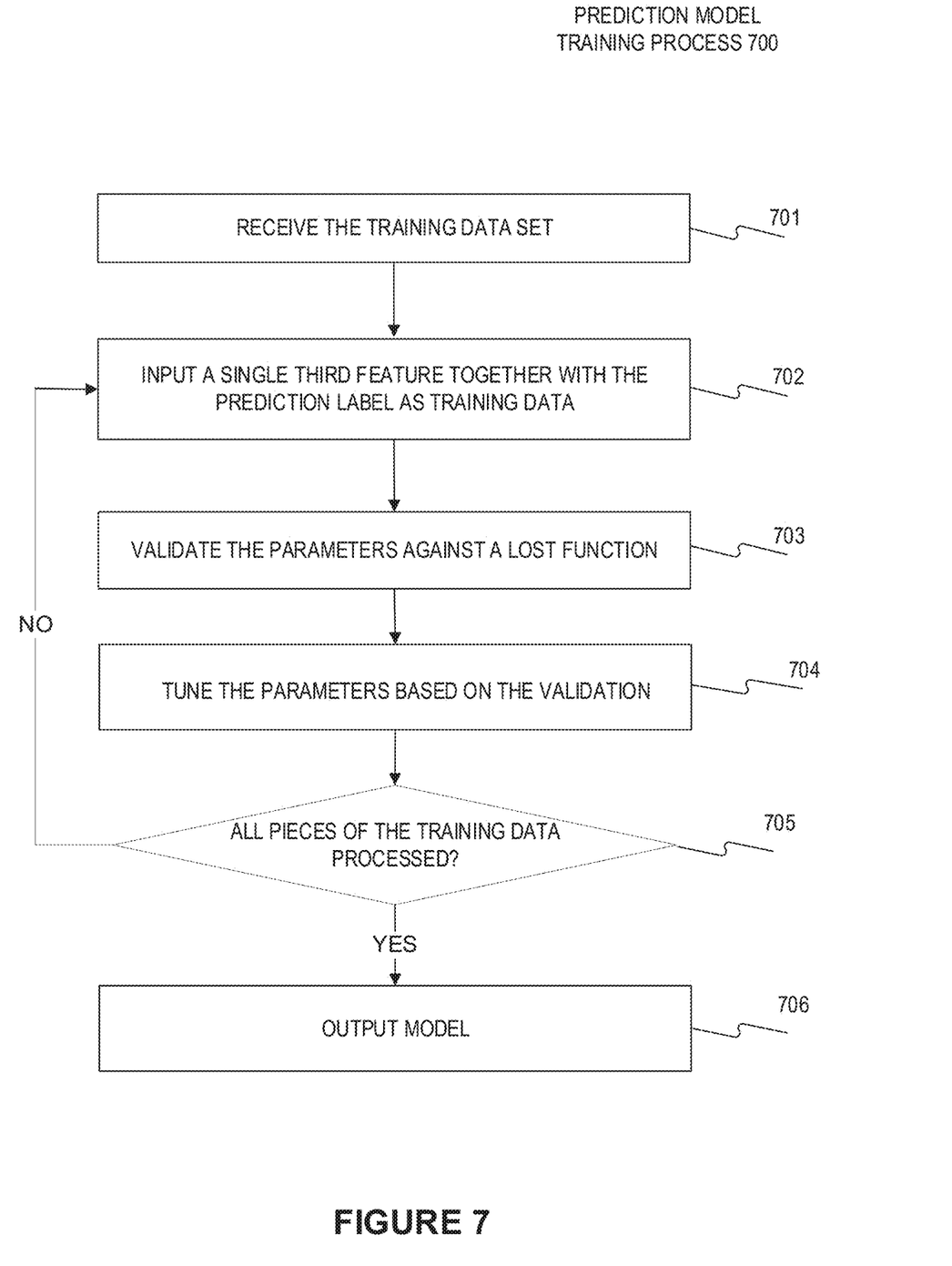
FIG. 7 illustrates the training process of the prediction model (CNN-sequence-to-sequence network learning network) according to an embodiment of present disclosure.

FIG. 7 illustrates the training process of the CNN-sequence-to-sequence network learning network according to an embodiment of present disclosure. As shown in FIG. 7, the prediction model training process 700 begins with receiving the training data set (step 701), each piece of which (i.e., each sample) comprised of a third feature (to be input into the CNN-sequence-to-sequence network learning network) at a position on a centerline of the vessel as well as the FFR value at the corresponding position (as the training label). Particularly, both the definition of the third feature and its inputting position may depend on the particular prediction model. For example, for the prediction model as shown in FIG. 2, the third feature may be constructed by concatenating at least one structural feature and a flow speed at the corresponding position on the centerline and may be input as a whole into the CNN. For another example, for the prediction model as shown in FIG. 5, the third feature may be constructed by an image patch at a position on the centerline, which may be input into the CNN to obtain the corresponding structure-related feature, and the flow speed at the corresponding position, which may be fused with the corresponding structure-related feature and input into the sequence-to-sequence network. Then, at step 702, a single third feature together with the corresponding prediction label, i.e., the FFR value, is input into the CNN-sequence-to-sequence network learning network as training data. In some embodiments, the weights of the whole learning network may have been initialized. At step 703, the parameters of the learning network may be validated against a lost function. Then at step 704, the parameter of the learning network may be tuned on the basis of the validation result at step 703. In some embodiments, steps 703 and 704 may also be integrated in the same step, wherein the parameters of the learning network may be optimized against a lost function on the basis of each piece of training data. In some embodiments, the optimization process may be performed by any one of the common algorithms, including but not limited to the gradient descent algorithm (such as standard stochastic gradient descent algorithm), Newton's method, conjugate gradient algorithm, quasi Newton method, and Levenberg Marquardt algorithm, etc.

In some embodiments, various lost functions, including but not limited to cross-entropy, absolute lost function, etc., may be adopted at step 703. For example, the loss function $J(\theta)$ may be defined as mean square error (MSE) as shown in Formula 1.

$$J(\theta) = \frac{1}{N} \sum_{i=1}^{N} (y_i - \hat{y}_i)^2 \qquad \text{Formula 1}$$

Where $y_i$ is the ground truth label (training label) while $\hat{y}_i$ is the model prediction result, N represents the number of samples, $\theta$ represents model parameters.

At step 705, it determines whether all pieces of the training data are already processed, if so, then at step 706, the trained learning network with present optimized parameters is output as the trained prediction model. Otherwise, the process returns to step 702 to process a subsequent piece of training data, until all the pieces are processed.

Figure 8:
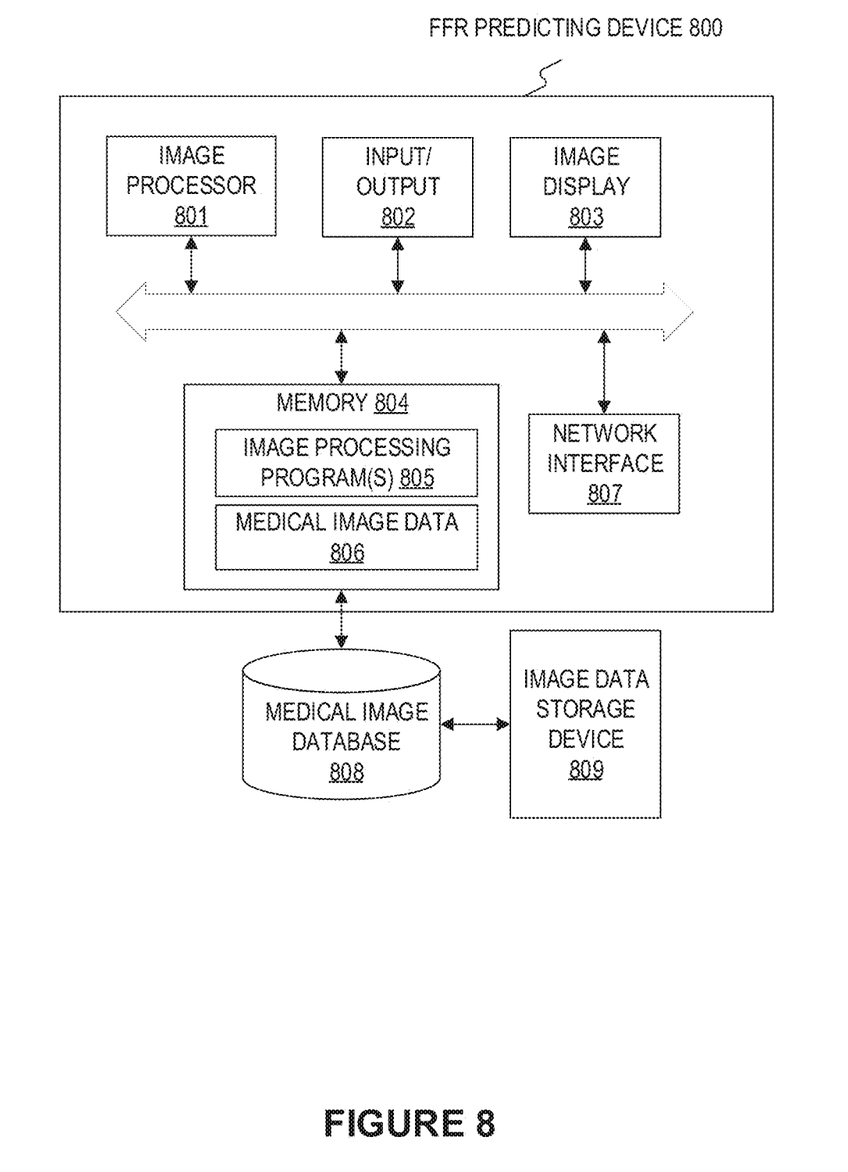
FIG. 8 illustrates a block diagram of an exemplary FFR predicting device according to an embodiment of present disclosure.

FIG. 8 illustrates a block diagram of an exemplary FFR predicting device according to an embodiment of present disclosure. The FFR predicting device 800 may include a network interface 807, by means of which the FFR predicting device 800 may be connected to the network (not shown), such as but not limited to the local area network in the hospital or the Internet. The network can connect the FFR predicting device 800 with external devices such as an image acquisition device (not shown), medical image database 808, and an image data storage device 809. An image acquisition device may be any type of imaging modalities, such as but not limited to CT, digital subtraction angiography (DSA), MRI, functional MRI, dynamic contrast enhanced-MRI, diffusion MRI, spiral CT, cone beam computed tomography (CBCT), positron emission tomography (PET), single-photon emission computed tomography (SPECT), X-ray, optical tomography, fluorescence imaging, ultrasound imaging, radiotherapy portal imaging.

In some embodiments, the FFR predicting device 800 may be a dedicated intelligent device or a general purpose intelligent device. For example, the device 800 may be a computer customized for image data acquisition and image data processing tasks, or a server placed in the cloud. For example, the device 800 may be integrated into the image acquisition device. Optionally, the device may include or cooperate with a 3D re-constructing unit for re-constructing the 3D model of the vessel on the basis of the 2D vessel images acquired by the image acquisition device.

The FFR predicting device 800 may include an image processor 801 and a memory 804, and may additionally include at least one of an input/output 802 and an image display 803.

The image processor 801 may be a processing device that includes one or more general processing devices, such as a microprocessor, a central processing unit (CPU), a graphics processing unit (GPU), and the like. More specifically, the image processor 801 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The image processor 801 may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the image processor 801 may be a special-purpose processor, rather than a general-purpose processor. The image processor 801 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The image processor 801 may also include graphical processing units such as a GPU from the GeForce®, Quadro®, Tesla® family manufactured by Nvidia™, GMA, Iris™ family manufactured by Intel™, or the Radeon™ family manufactured by AMD™. The image processor 801 may also include accelerated processing units such as the Desktop A-4 (6, 8) Series manufactured by AMD™, the Xeon Phi™ family manufactured by Intel™. The disclosed embodiments are not limited to any type of processor(s) or processor circuits otherwise configured to meet the computing demands of identifying, analyzing, maintaining, generating, and/or providing large amounts of imaging data or manipulating such imaging data to provide FFR prediction, or to manipulate any other type of data consistent with the disclosed embodiments. In addition, the term "processor" or "image processor" may include more than one processor, for example, a multi-core design or a plurality of processors each having a multi-core design. The image processor 801 can execute sequences of computer program instructions, stored in memory 804, to perform various operations, processes, methods disclosed herein.

The image processor 801 may be communicatively coupled to the memory 804 and configured to execute computer-executable instructions stored therein. The memory 804 may include a read only memory (ROM), a flash memory, random access memory (RAM), a dynamic random-access memory (DRAM) such as synchronous DRAM (SDRAM) or Rambus DRAM, a static memory (e.g., flash memory, static random access memory), etc., on which computer executable instructions are stored in any format. In some embodiments, the memory 804 may store computer-executable instructions of one or more image processing program(s) 805. The computer program instructions can be accessed by the image processor 801, read from the ROM, or any other suitable memory location, and loaded in the RAM for execution by the image processor 801. For example, memory 804 may store one or more software applications. Software applications stored in the memory 804 may include, for example, an operating system (not shown) for common computer systems as well as for soft-controlled devices. Further, memory 804 may store an entire software application or only a part of a software application (e.g. the image processing program (s) 805) to be executable by the image processor 801. In addition, the memory 804 may store a plurality of software modules, for implementing the respective steps of the method for automatically predicting FFR based on images of a vessel or the process for training the FFR predicting model consistent with the present disclosure. For example, the FFR prediction model training unit 302, the FFR prediction unit 303, the training data generating unit 309, the second feature extracting unit 308 (including the flow speed calculating unit 304, the stereo-reconstruction unit 305, and the fusing unit 307), as shown in FIG. 3, may be implemented as soft modules stored on the memory 804. For another example, at least the FFR prediction unit 303 and the second feature extracting unit 308 are implemented as soft modules stored on the memory 804, the FFR prediction model training unit 302 may be located remote from the FFR predicting device 800 and communicate with the FFR prediction unit 303 to enable it receive the FFR prediction model, which is already trained by the FFR prediction model training unit 302 with the training data from the training data generating unit 309 or the training data database 301, for predicting FFR values on the 3D centerline of the vessel. For another example, the FFR prediction model training unit 602, the FFR prediction unit 603 (including the fusing unit 607), the training data generating unit 609, the flow speed calculating unit 604, and the image patch extracting unit 605, as shown in FIG. 6, may be implemented as soft modules stored on the memory 804. For still another example, at least the FFR prediction unit 603, the flow speed calculating unit 604, and the image patch extracting unit 605 are implemented as soft modules stored on the memory 804, the FFR prediction model training unit 602 may be located remote from the FFR predicting device 800 and communicate with the FFR prediction unit 603 to enable it receive the FFR prediction model, which is already trained by the FFR prediction model training unit 602 with the training data from the training data generating unit 609 or the training data database 601, for predicting FFR values on the 2D centerline of the vessel.

Besides, the memory 804 may store data generated/buffered when a computer program is executed, for example, medical image data 806, including the medical images transmitted from image acquisition device(s), medical image database 808, image data storage device 809, etc. Such medical image data 806 may include the received vessel image(s) for which the automatic feature extraction and further FFR prediction are to be implemented by the image processing program(s) 805. Besides, the medical image data 806 may also include the actually extracted and input features together with the corresponding FFR prediction results. The image processor 801 may execute the image processing program(s) 805 to implement a method for automatically predicting FFR based on images of a vessel. In some embodiments, when executing the image processing program(s) 805, the image processor 801 may associate the corresponding input features with the prediction results, and transmit the same into the memory 804 so as to maintain the same as the medical image data 806. Optionally, the memory 804 may communicate with the medical image database 808 to obtain vessel images therefrom or to transmit the vessel images together with the corresponding intermediate information for FFR prediction to and thus stored on the medical image database 808, to be accessed, obtained, and utilized by other FFR predicting devices, if needed. In some embodiments, as shown in FIG. 3, the intermediate information may include but is not limit to any one of the parameters of the trained prediction model, the sequence of second feature, the sequence of flow speeds, the 3D vessel model, the sequence of structural features, and the sequence of positions on the 3D centerline. In some embodiments, as shown in FIG. 6, the intermediate information may include but is not limit to any one of the parameters of the trained prediction model, the sequence of image patches, the sequence of flow speeds, and the sequence of positions on the 2D centerline.

In some embodiments, the FFR prediction model (especially the CNN-sequence-to-sequence network learning network) may be stored in the memory 804. Optionally, the learning network may be stored in a remote device, a separate database, such as the medical image database 808, distributed devices, and may be used by the image processing program(s) 805. The actually input features together with the prediction results may be stored as new training samples in the medical image database 808, so as to update the training data set continuously and improve the performance of the trained learning network continuously. Besides, the parameters of the previously trained prediction model stored on the medical image database 808 may be adopted as initial parameters of the prediction model during later training, which may accelerate the training process substantially.

In some embodiments, the image data storage device 809 may be provided to exchange image data with the medical image database 808. For example, the image data storage device 809 may reside in other medical image acquisition devices.

The input/output 802 may be configured to allow the FFR predicting device 800 to receive and/or send data. The input/output 802 may include one or more digital and/or analog communication devices that allow the device 800 to communicate with a user or other machine and device. For example, the input/output 802 may include a keyboard and a mouse that allow the user to provide an input.

The network interface 807 may include a network adapter, a cable connector, a serial connector, a USB connector, a parallel connector, a high-speed data transmission adapter such as optical fiber, USB 8.0, lightning, a wireless network adapter such as a Wi-Fi adapter, a telecommunication (8G, 4G/LTE, etc.) adapters. The device 800 may be connected to the network through the network interface 807. The network may provide the functionality of local area network (LAN), a wireless network, a cloud computing environment (e.g., software as a service, platform as a service, infrastructure as a service, etc.), a client-server, a wide area network (WAN), and the like.

Besides displaying the medical images, the image display 803 may also display other information, such as the predicted FFR values by mapping back the same to the 2D centerline or to the 3D vessel geometry. For example, the image display 803 may be an LCD, a CRT, or an LED display.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in computer readable storage medium, and when executed, may cause a machine to perform the described functions or operations and include any mechanism for storing information in the form accessible by a machine (e.g., computing device, electronic system, etc.), such as recordable or non-recordable media (e.g., read-only memory (ROM), random access memory (RAM), disk storage media, optical storage media, flash memory devices, etc.).

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Exemplary Methods described herein can be machine or computer-implemented at least in part. Some examples can include a computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for automatically predicting a physiological parameter based on images of a vessel, comprising:
    receiving the images of the vessel acquired by an imaging device;
    determining, by a processor, a sequence of flow features at a sequence of positions on a centerline of the vessel based on the images of the vessel;
    determining, by the processor, a sequence of structure-related features at the sequence of positions on the centerline of the vessel;
    fusing, by the processor, the sequence of structure-related features and the sequence of flow features at the sequence of positions respectively; and
    determining, by the processor, the physiological parameter for the vessel at the sequence of positions, by using a sequence-to-sequence neural network configured to capture sequential dependencies among the sequence of fused features.

2. The computer-implemented method of claim 1, wherein determining the sequence of structure-related features further comprises:
    extracting the centerline of the vessel from the images of the vessel;
    sampling a sequence of fixed sized image patches at the sequence of positions on the centerline of the vessel; and
    applying a convolutional neural network to the sequence of fixed sized image patches at the sequence of positions on the centerline of the vessel to obtain the sequence of the structure-related features at the sequence of positions on the centerline of the vessel.

3. The computer-implemented method of claim 1, wherein the structure-related feature at each position on the centerline of the vessel includes at least one of vessel radius, reference radius, curvature, and depth of optical path at the corresponding position.

4. The computer-implemented method of claim 1, wherein determining the sequence of flow-related features further comprises determining flow speeds at the sequence of positions on the centerline of the vessel.

5. The computer-implemented method of claim 1, wherein fusing the sequence of structure-related features and the sequence of flow features comprises concatenating the structure-related feature and the flow feature at a corresponding position on the centerline of the vessel.

6. The computer-implemented method of claim 1, wherein fusing the sequence of structure-related features and the sequence of flow features comprises applying a convolutional neural network to the sequence of structure-related features and the sequence of flow features to obtain the sequence of fused features at the sequence of positions on the centerline of the vessel.

7. The computer-implemented method of claim 6, wherein the convolutional neural network and the sequence-to-sequence neural network are trained integrally.

8. The computer-implemented method of claim 1, wherein the sequence-to-sequence neural network is trained using training data generated by correcting simulated values of the physiological parameter by measured values of the physiological parameter.

9. The computer-implemented method of claim 8, wherein correcting the simulated values of the physiological parameter by measured values of the physiological parameter comprises modifying the simulated values of the physiological parameter to make the simulated value at a measurement point on the centerline equal to the corresponding measured value at the measurement point while maintaining varying rates of a gradient of the simulated values of the physiological parameter.

10. The computer-implemented method of claim 1, wherein the sequence-to-sequence neural network is selected from a group of a recurrent neural network, gated recurrent unit, long short-term memory unit or their bidirectional variants.

11. The computer-implemented method of claim 1, wherein the physiological parameter is an FFR associated with the vessel.

12. A system for automatically predicting a physiological parameter based on images of a vessel, comprising:
   an interface configured to receive the images of the vessel acquired by an imaging device; and
   a processor configured to:
      determine a sequence of flow features at a sequence of positions on a centerline of the vessel based on the images of the vessel;
      determine a sequence of structure-related features at the sequence of positions on the centerline of the vessel;
      fuse the sequence of structure-related features and the sequence of flow features at the sequence of positions respectively; and
      determine the physiological parameter for the vessel at the sequence of positions, by using a sequence-to-sequence neural network configured to capture sequential dependencies among the sequence of fused features.

13. The system of claim 12, wherein an imaging modality of the imaging device is selected from a group of CT, digital subtraction angiography (DSA), MRI, functional MRI, dynamic contract enhanced-MRI, diffusion MRI, spiral CT, cone beam computed tomography (CBCT), positron emission tomography (PET), single-photon emission computed tomography (SPECT), X-ray, optical tomography, fluorescence imaging, ultrasound imaging, radiotherapy portal imaging.

14. The system of claim 12, wherein the structure-related feature at each position on the centerline of the vessel includes at least one of vessel radius, reference radius, curvature, and depth of optical path at the corresponding position.

15. The system of claim 12, wherein flow feature at each position on the centerline of the vessel comprises a flow speed at the corresponding position.

16. The system of claim 12, the sequence-to-sequence neural network is trained using training data generated by correcting simulated values of the physiological parameter by measured values of the physiological parameter.

17. The system of claim 12, wherein the physiological parameter is an FFR associated with the vessel.

18. A non-transitory computer readable medium having instructions stored thereon, the instructions, when executed by a processor, perform a method for automatically predicting a physiological parameter based on images of a vessel, the method comprising:
   receiving the images of the vessel acquired by an imaging device;
   determining a sequence of flow features at a sequence of positions on a centerline of the vessel based on the images of the vessel;
   determining a sequence of structure-related features at the sequence of positions on the centerline of the vessel;
   fusing the sequence of structure-related features and the sequence of flow features at the sequence of positions respectively; and
   determining the physiological parameter for the vessel at the sequence of positions, by using a sequence-to-sequence neural network configured to capture sequential dependencies among the sequence of fused features.

19. The non-transitory computer readable medium of claim 18, wherein determining the sequence of flow features further comprises determining flow speeds at the sequence of positions on the centerline of the vessel.

20. The non-transitory computer readable medium of claim 18, fusing the sequence of structure-related features and the sequence of flow features comprises concatenating the structure-related feature and the flow feature at a corresponding position on the centerline of the vessel.

* * * * *